US00PP09807P

United States Patent [19]

van der Meer

[11] Patent Number: Plant 9,807

[45] Date of Patent: Feb. 18, 1997

[54] HYBRID TEA ROSE PLANT NAMED 'SELANTIMOON'

[75] Inventor: Peter J. A. van der Meer, Uithoorn, Netherlands

[73] Assignee: Terra Nigra Holding B.V., De Kwakel, Netherlands

[21] Appl. No.: 591,386

[22] Filed: Jan. 25, 1996

[51] Int. Cl.[6] ..... A01H 5/00

[52] U.S. Cl. ..... Plt./18

[58] Field of Search ..... Plt./16, 18, 19

[56] References Cited

U.S. PATENT DOCUMENTS

P.P. 9,184 4/1995 van der Meer ..... Plt./18

*Primary Examiner*—Howard J. Locker

[57] ABSTRACT

A new rose variety of the Hybrid Tea class, characterized by its continuous production of large pink flowers, borne singly on upright stems on a bush of medium height, having glossy foliage and a mild honey-like fragrance.

2 Drawing Sheets

BACKGROUND OF THE INVENTION

The present invention relates to a new and distinct variety of rose plant of the Hybrid Tea class, which was originated by me by crossing the variety 'Jacaranda' with an unnamed seedling (SR 80.077).

The primary objective of this breeding was to obtain a new large type rose with a good presentation and bud shape in different colors. Among the novel characteristics possessed by the new variety which distinguish it from its parents and all other varieties of which I am aware are:

(1) A large typically pink flower;

(2) Rapid flowering cycles;

(3) Highly glossy foliage;

(4) A vigorous upright plant of medium height; and (5) A plant which has very few prickles on the rachis.

Asexual reproduction of the new rose variety by cutting and grafting using Nathal Briar as rootstock, as performed in a greenhouse in De Kwakel, The Netherlands, shows that the aforementioned characteristics and distincions come true to form and are established and transmitted through succeeding propagations.

BRIEF DESCRIPTION OF THE DRAWINGS

The new variety of rose plant is illustrated by the accompanying photographic illustrations, of which:

Sheet 1 shows a full face view of the flower; and

Sheet 2 shows typical specimens of the vegetative growth and flowers of the new variety in different stages of development and as depicted in color as nearly true as it reasonably possible to make the same illustration of this character.

The following is a detailed description of this new variety, with color terminology in accordance with The Royal Horticultural Society Colour Chart (R.H.S.C.C.). The terminology used in the color description herein refers to plate numbers in the aforementioned color chart e.g. "55C" is plate "55C" of The Royal Horticultural Society Colour Chart.

Parentage: Seedling.

*Seed parent.*—'Jacaranda'.

*Pollen parent.*—Unnamed seedling (SR 88.077).

Classification:

*Botanic.*—Hybrid Tea.

*Commercial.*—Hybrid Tea.

BOTANICAL DESCRIPTION OF THE PLANT

FLOWER (Observations made from specimens grown in a greenhouse at De Kwakel, The Netherlands)

Blooming habit of Selantimoon: Continuous.

A. Bud:

(1) *Size.*—Medium. Diameter 2.5–3.0 cm. Length 3.5–4.0 cm.

(2) *Form.*—Egg shaped (oval, pointed); is not affected by wet or hot weather.

(3) *Color.*—When the sepals first divide, the color of the outside is pink 58D.

(4) *Sepals.*—Shape; 30 to 32 mm in length. Slightly branched, curl back when petals start to unfurl. Color: inside: 143B. outside: 141C flushed 59B. Cotton matting on inner surface, fine hairs on outer surface.

(5) *Phyllaries.*—Number: very few. Shape: small. Color: 143B.

(6) *Calyx.*—Color: 141C. Shape: pear. Size: broad. Aspect: hairy. Odor when rubbed: slightly present.

(7) *Rate of opening.*—Normal (8) *Peduncle.*—Length: long, 8 to 10 cm. Aspect: hairy, hardly any prickles. Strength: strong. Color: 146A+146B.

(8) *Openings.*—Opens up well; is not affected by adverse weather.

B. Bloom:

(1) *Size.*—Large; when fully expanded about 12 cm in diameter with a depth of about 5 cm.

(2) *Borne.*—Single.

(3) *Stems.*—Length: long. Strength: strong.

(4) *Form (when first open).*—Cupped. Permanence: will flatten when aging.

(5) *Petalage.*—Number of petals: average 30.

(6) *Color.*—Center of flower: 55C. Outer petals: 62D+62D. Base of petals: 56C with a small yellow spot at the base 1C. Inside of petals: 55C. Reverse of petals: 55C+62D. General tonality: 55C.

(7) Discoloration.—General tonality 55C aging to 56D.

C. Petals:

(1) *Texture.*—Soft; is not affected by wet or hot weather.

(2) *Appearance.*—Inside: shiny. Outside: satiny.

(3) *Form.*—Oval-round shaped. Medium undulation of margin.
(4) *Arrangement.*—Regular informal.
(5) *Petaloids in center.*—Number: average 6. Size: small. Color: base 2C, middle and marginal zone 56A flushed 63B.
(6) *Persistence.*—Drop off cleanly.
(7) *Fragrance.*—Medium; honey-like scent.
(8) *Lasting quality.*—On the plant: good. As cutflower: moderate, 9 days on Chrysal RVB. On the plant: good.

REPRODUCTIVE ORGANS

A. Stamens:
(1) *Arrangement.*—Regularly arranged around styles.
(2) *Number.*—Average close to 150.
(3) *Length.*—10 to 15 mm.
(4) *Anthers.*—Size: medium, 3 to 5 mm. Color: 19A+ 11C.
(5) *Filaments.*—Length: medium, 8 to 10 mm. Color: base of anthers 56D, lower filament 63A.
(6) *Pollen.*—Color: 19A.

B. Pistils:
(1) *Styles.*—Number: average close to 150. Length: 8 to 12 mm. Color: 57A with white hairs at base.
(2) *Stigmas.*—Color: 7A.
(3) *Fruit.*—Unknown.

PLANT

A. Form: Bed rose.
B. Growth: Upright.
C. Height: Medium, 120 to 150 cm.
D. Foliage: Compound of 3 to 5 leaflets. Average 8 to 10 compound leaves on bloom stem, 10 to 12 on main canes.
(1) *Size.*—Medium.
(2) *Quantity.*—Average, stems well covered.
(3) *Color.*—New foliage: upper side: 147A. under side: 138B. Old foliage: upper side: 139A. under side: 138B.
(3) *Texture.*—Upper side: glossy, leathery. Under side: dull, leathery.
(4) *Terminal leaflet.*—Shape: oval, base rounded. Size: large. Length 65 to 70 mm. Diameter 50 mm. Length petiole 15 to 20 mm.
(5) *Ribs and veins.*—Ordinary.
(6) *Rachis.*—Upper side: slight glandular hair. Lower side: very few 1 to 2 mm sized hooked prickles, 1 to 5 per compound leaf.
(7) *Margin type.*—Slightly serrate, 3 points/cm 1½ mm peak.
(8) *Stipules.*—Length: average 15 mm, auricle to 5 mm. Texture: smooth, glandular hairs at outer edge. Color: reddish brown 183A.

E. Resistance to diseases Medium.

F. Wood:
(1) *New wood.*—Color: reddish brown. Bark: smooth.
(2) *Old wood.*—Color: green. Bark: smooth.

G. Thorns:
(1) *Quantity.*—On main stalks from base: medium. On laterals from stalk: medium.
(2) *Form.*—Deep concave.
(3) *Length.*—Large.
(4) *Hooked.*—Downward.
(5) *Color (when young).*—Reddish brown.
(6) *Position.*—Irregular.

H. Prickles:
*Quantity.*—On peduncle: absent or very few. On rachis: very few.

I. Short needles:
*Quantity.*—Absent or very few.

I claim:

1. A new and distinct variety of rose plant of the Hybrid Tea class, substantially as herein shown and described characterized particularly as to novelty by its large pink flowers, borne singly on strong, upright stems with glossy foliage and its mild honey-like fragrance.

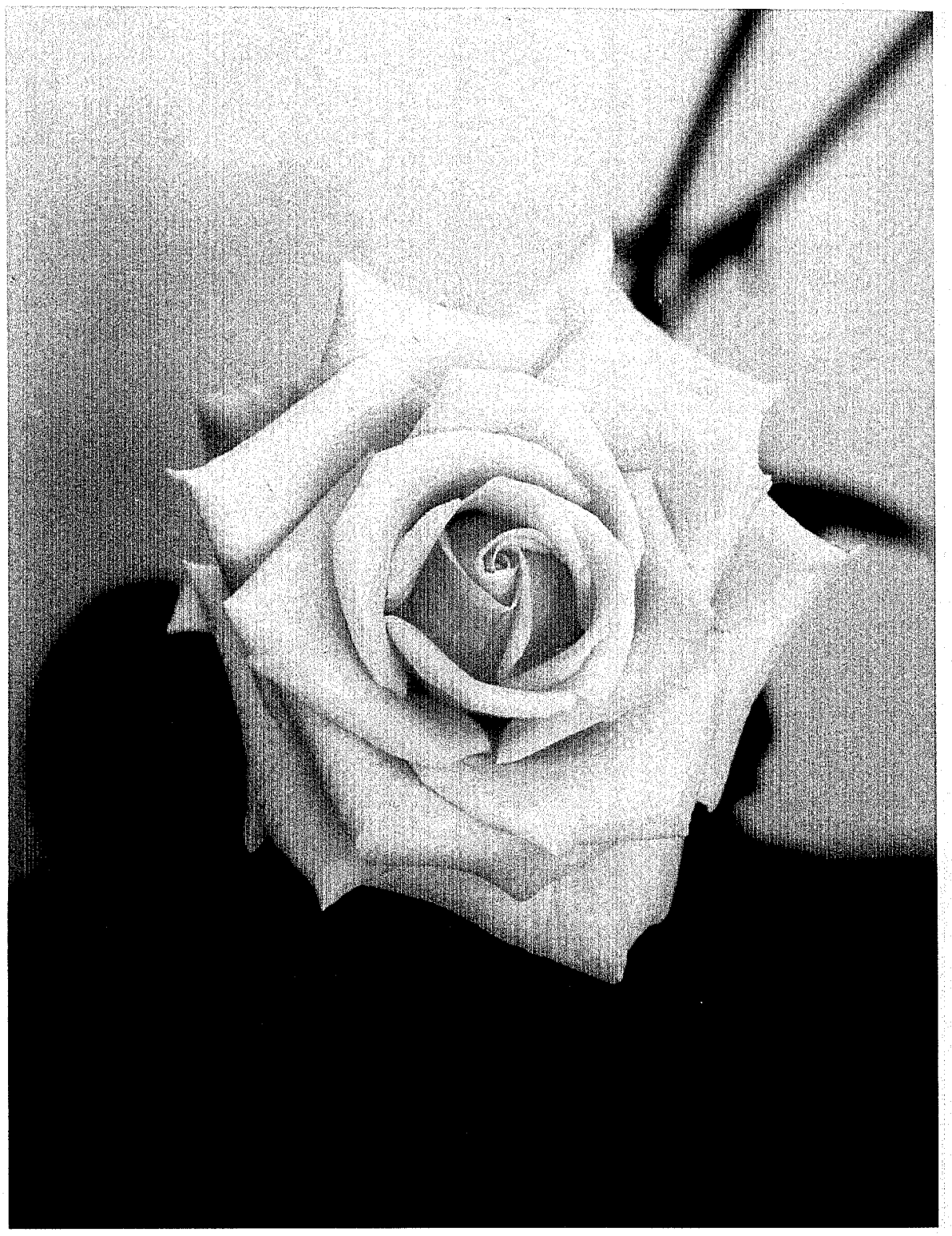

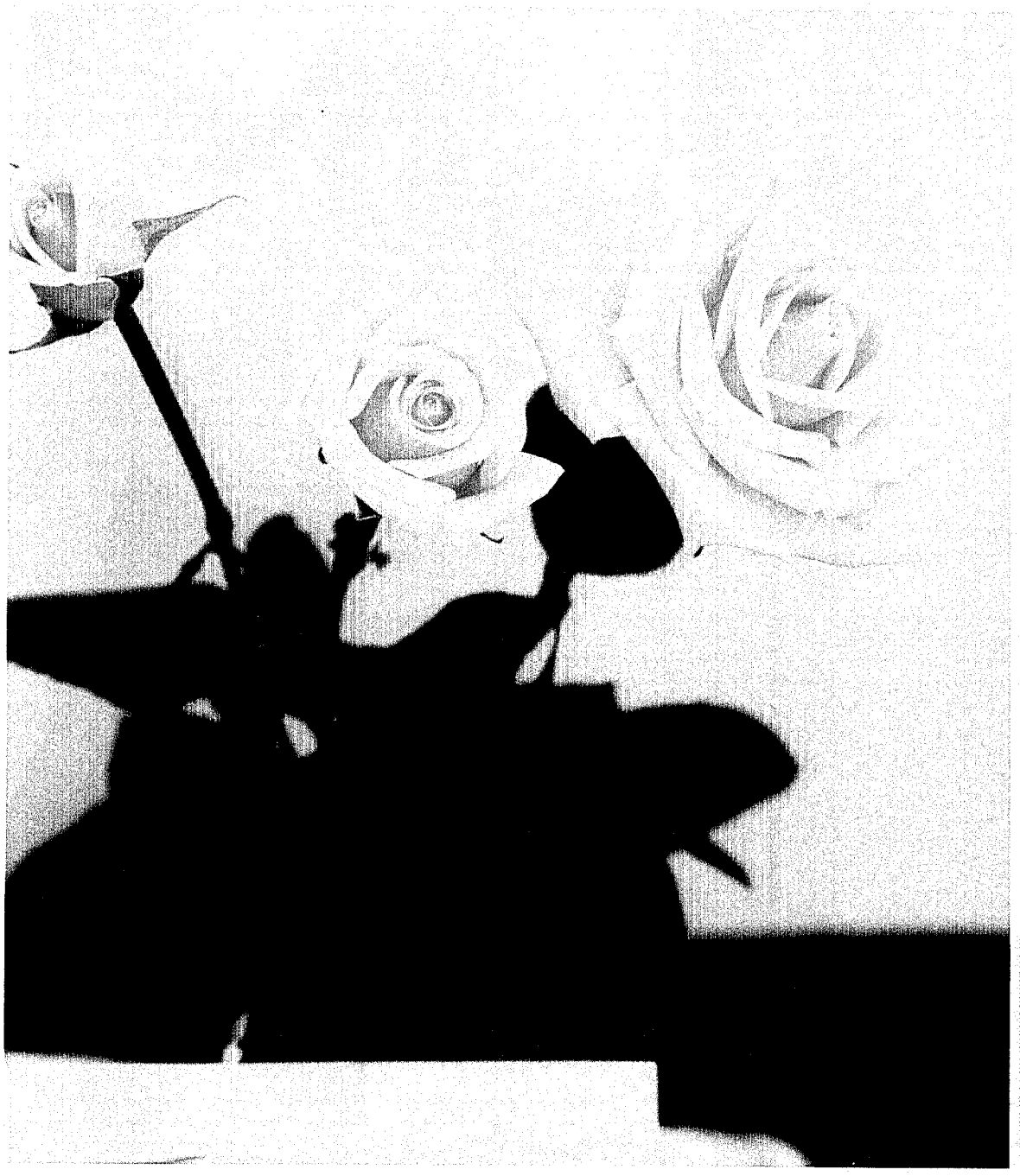

* * * * *